(12) United States Patent
Yuyama et al.

(10) Patent No.: US 9,641,812 B2
(45) Date of Patent: May 2, 2017

(54) DISPENSING VERIFICATION DEVICE (75) Inventors: Hiroyuki Yuyama, Osaka (JP); Keita Yasuoka, Osaka (JP)

(73) Assignee: YUYAMA MFG. CO., LTD., Osaka (JP)

(*) Notice: Subject to any disclaimer, the term of this patent is extended or adjusted under 35 U.S.C. 154(b) by 625 days.

(21) Appl. No.: 13/984,787

(22) PCT Filed: Feb. 8, 2012

(86) PCT No.: PCT/JP2012/052823
§ 371 (c)(1),
(2), (4) Date: Aug. 9, 2013

(87) PCT Pub. No.: WO2012/111498
PCT Pub. Date: Aug. 23, 2012

(65) Prior Publication Data
US 2013/0314535 A1  Nov. 28, 2013

(30) Foreign Application Priority Data
Feb. 14, 2011 (JP) .................... 2011-028436

(51) Int. Cl.
*H04N 9/47* (2006.01)
*H04N 7/18* (2006.01)
(Continued)

(52) U.S. Cl.
CPC ............. *H04N 7/188* (2013.01); *G06K 9/00* (2013.01); *G06Q 50/22* (2013.01);
(Continued)

(58) Field of Classification Search
None
See application file for complete search history.

(56) References Cited

U.S. PATENT DOCUMENTS

| | | | |
|---|---|---|---|
| 2007/0225574 A1* | 9/2007 | Ueda | A61B 5/00 600/300 |
| 2008/0306766 A1* | 12/2008 | Ozeki | G06F 19/321 705/2 |
| 2012/0081551 A1* | 4/2012 | Mizuno | H04N 7/185 348/150 |

FOREIGN PATENT DOCUMENTS

| | | |
|---|---|---|
| JP | 2006-163821 A | 6/2006 |
| JP | 2006-187406 A | 7/2006 |

(Continued)

OTHER PUBLICATIONS

International Search Report for PCT/JP2012/052823, mailed Jun. 26, 2012, 4 pages (in Japanese).

(Continued)

*Primary Examiner* — Dakshesh Parikh
(74) *Attorney, Agent, or Firm* — Jones Day (57) ABSTRACT

A dispensing verification device which is capable of readily verifying the contents of dispensing. The dispensing verification device has a camera capturing a counter with a mark, an image management server storing the image captured by the camera, a determination means determining whether the mark is hidden by a prescription, a timer outputting a time information, a writing control means controlling the writing of the image to the image management server, a display displaying the image stored in the image management server, and a readout control means retrieving a written image and reading out the written image from the image management server and outputting the same to the display. If the determination means determines that the mark is hidden, the writing control means associates the image captured by the camera with the time information and writes the image to the image management server as a still image.

18 Claims, 10 Drawing Sheets

(51) Int. Cl.
*G06Q 50/22* (2012.01)
*G07F 17/00* (2006.01)
*H04N 5/232* (2006.01)
*H04N 5/77* (2006.01)
*G06K 9/00* (2006.01)

(52) U.S. Cl.
CPC ......... *G07F 17/0092* (2013.01); *H04N 5/232* (2013.01); *H04N 5/77* (2013.01)

(56) References Cited

FOREIGN PATENT DOCUMENTS

| | | | | |
|---|---|---|---|---|
| JP | 2008-65596 | A | 3/2008 | |
| JP | 4276654 | B2 | 6/2009 | |
| JP | 2010-86257 | A | 4/2010 | |
| JP | WO 2010123138 | A1 * | 10/2010 | ............ H04N 7/181 |
| JP | 2010-258729 | A | 11/2010 | |
| WO | WO 2004/112685 | A1 | 12/2004 | |

OTHER PUBLICATIONS

Written Opinion for PCT/JP2012/052823, mailed Apr. 26, 2012, 3 pages (in Japanese).

* cited by examiner

PRESCRIPTION (This prescription is valid in every insurance pharmacy.)

| No. of Public expense defrayer | | | | | | | No. of Insurer | | | | | | | |
|---|---|---|---|---|---|---|---|---|---|---|---|---|---|---|
| No. of Claimant of medical care at public expense | | | | | | | Sym., No. of Certificate or notebook for the insured | | | | | | | |

| Patient | Name | | | | Location and name of insurance medical institute |
|---|---|---|---|---|---|
| | Birth date | yy/mm/dd | Male/Female | | Phone No. |
| | Classification | The insured | Dependent | | Insurer's name |

(seal)

| Issue date | yy/mm/dd | Validity period of prescription | yy/mm/dd |
|---|---|---|---|

| Prescription | |
|---|---|

| Remark | |
|---|---|

If it is impossible to change to generic medicine, please sign below

Signature of insurance doctor

| Dispensing request date | yy/mm/dd | No. of Public expense defrayer | | | | | | | |
|---|---|---|---|---|---|---|---|---|---|
| Location and name of insurance institute Insurance pharmacist's name | (seal) | No. of Claimant of medical care at public expense | | | | | | | |

FIG. 6

Dispensing verification system

| | | | | |
|---|---|---|---|---|
| A yama ichiro 09:00:30 ~ 09:03:27 | A kawa ichiro 09:11:21 ~ 09:15:15 | A da ichiro 09:16:21 ~ 09:25:05 | A ki hanako 09:17:00 ~ 09:19:55 | A moto ichiro 09:21:31 ~ 09:25:15 |
| B yama jiro 09:26:31 ~ 09:31:12 | B kawa jiro 09:27:21 ~ 09:30:21 | B da tsukiko 09:11:28 ~ 09:35:17 | B ki tsukiko 09:50:11 ~ 09:51:56 | B moto jiro 10:01:45 ~ 10:03:45 |
| C yama saburo 10:11:02 ~ 10:13:05 | C kawa saburo 10:12:21 ~ 10:16:21 | C da seiko 10:21:35 ~ 10:24:19 | C ki seiko 10:26:21 ~ 10:35:15 | C moto saburo 10:45:32 ~ 10:47:42 |

Specified date 2011/02/01   Start time 09:00

Previous page   Next page   Moving image playback

FIG. 7

Let's use medicine correctly

| Date | Medicine |
|---|---|

TAIYO, Hanako
☐ 01/06/31 Sun Clinic   Dr. TAIYO, Jyunichi
○○○ 100mg  Five per day   Medicine for enhancing blood circulation
                          Medicine for decreasing cholesterol
    Three times per day  14 day dosage  After every meal
○○○ 250mg  Five per day   Medicine for suppressing bacterial infection
    Three time per day   14 day dosage  After every meal
○○○   5g in total   Inflammation suppression  Eczema dermatitis cure
    Three times per day   Application
○○○   3g per day   Medicine for replenishing vitamin deficiency
    Three times per day   5 day dosage  After every meal
                          Taiyo Pharmacy
                          TEL 0728-75-7300

Medicine notebook

When going to pharmacy, please make
sure to bring this notebook with you

Name  TAIYO, Hanako

No.

yy/mm/dd ~ yy/mm/dd

This notebook contains your records.  Please ensure
safekeeping of this notebook

FIG. 8

| | Medicine Name | Flomox tablet 100mg | | | | | |
|---|---|---|---|---|---|---|---|
|  | Usage | Three times, Dose after every meal | | | | | |
| | Number of dates/times | After rising | Morning | Afternoon | Evening | Before sleeping | One dosage |
| | 5 | | 1 tablet | 1 tablet | 1 tablet | | 1 tablet |
| efficacy · effect | ·This medicine kills germs and cures infection. | | | | | | |
| Warning | | | | | | | |

| | Medicine Name | Loxonin tablet 60mg | | | | | |
|---|---|---|---|---|---|---|---|
|  | Usage | Three times, Dose after every meal | | | | | |
| | Number of dates/times | After rising | Morning | Afternoon | Evening | Before sleeping | One dosage |
| | 5 | | 1 tablet | 1 tablet | 1 tablet | | 1 tablet |
| efficacy · effect | ·This medicine suppresses pain or inflammation or alleviates fever. | | | | | | |
| Warning | · Please make sure to ask a doctor if you have had asthma after taking aspirin, other antifebrile or analgesic, etc.<br>· Please take this medicine after or immediately after a meal to prevent stomach irritation. | | | | | | |

| | Medicine Name | Selbex capsule 50mg | | | | | |
|---|---|---|---|---|---|---|---|
|  | Usage | Three times, Dose after every meal | | | | | |
| | Number of dates/times | After rising | Morning | Afternoon | Evening | Before sleeping | One dosage |
| | 5 | | 1 capsule | 1 capsule | 1 capsule | | 1 capsule |
| efficacy · effect | · This medicine protects gastric mucous membrane and reconstructs stomach tissue | | | | | | |
| Warning | | | | | | | |

| | Medicine Name | Transamin capsule 250mg | | | | | |
|---|---|---|---|---|---|---|---|
|  | Usage | Three times, Dose after every meal | | | | | |
| | Number of dates/times | After rising | Morning | Afternoon | Evening | Before sleeping | One dosage |
| | 5 | | 1 capsule | 1 capsule | 1 capsule | | 1 capsule |
| efficacy · effect | · This medicine stops bleeding. This medicine suppresses allergies such as urticarial, eczema, etc. This medicine suppresses pain or inflammation of the throat. This medicine is for canker sore. | | | | | | |
| Warning | | | | | | | |

Regarding medicine   Name   January 11, 2011   Clinic   TEL 06-6865-1001

DISPENSING VERIFICATION DEVICE

CROSS-REFERENCE TO RELATED APPLICATIONS

This application is a 35 U.S.C. §371 national stage filing of International Application No. PCT/JP2012/052823, filed on Feb. 8, 2012, which claims the benefit of Japanese Patent Application No. 2011-028436, filed on Feb. 14, 2011, the entire contents of both of which are incorporated by reference in their entireties.

TECHNICAL FIELD

The present invention relates to dispensing verification device that is capable of readily verifying the contents of the medicine dispensed in pharmacies at a later date by using a moving image or a still image obtained from a camera.

BACKGROUND

At in-hospital pharmacies and out-of-hospital pharmacies, patients having received a medicine make inquiries at a later date as to whether the medicine received from the pharmacies corresponds to the number and type that a doctor has prescribed.

No system existed in the past that was capable of objectively checking this type of information. Thus, it was impossible to determine whether the medicine was correctly administered to the patient.

Patent Document 1 proposes a system that captures the scene of a pharmacist providing medicine by a camera and checks at a later date whether the medicine was provided as prescribed.

According to the aforesaid system, an RFID tag is attached on a bottom of a carrier in which the medicines are provided. If the RFID tag of the carrier is moved into a capture range of the camera, then the system starts to record a moving image. If the RFID tag of the carrier is moved out of the capture range of the camera, then the system ceases to record the moving image. Further, the recorded moving image is associated with a recording time and the system is capable of checking the requested dispensing action by retrieving the moving images by date and time.

If using the aforesaid system, it is possible to verify whether the medicine was correctly dispensed when the patient makes the aforementioned inquiries, by retrieving the moving images by date and time where dispensing had occurred.

Patent Document 1: Japanese Patent No. 4276654

SUMMARY

The aforesaid system starts or stops photographing by receiving signals from the RFID tag.

Further, in dispensing pharmacies, tablets are packed by means of a tablet packing machine or the like. The tablet packing machine performs the packing process by receiving signals from an RFID tag and then obtaining information on packing tablets. There are malfunction concerns when the signal of the RFID tag of the tablet packing machine interferes with the signal of another RFID. Thus, it is undesirable to use various RFID tags in dispensing pharmacies.

The present invention has been made in light of the foregoing circumstances. It is an object of the present invention to provide a dispensing verification device which is capable of readily verifying the contents dispensed at a later date without using an RFID tag.

The present invention provides a dispensing verification device comprising: a camera capturing a counter at which a work is performed; a storage means storing an image captured by the camera; a determination means determining whether a dispensing-related target object exists on the counter; a timer means outputting a time information; a writing control means controlling the writing of an image to the storage means in response to an output of the determination means; a display means displaying the image stored in the storage means; and a readout control means retrieving the written image and reading out the written image from the storage means and outputting the written image to the display means. If it is confirmed by the determination means that the dispensing-related target object exists, the writing control means associates the image captured by the camera with the time information of the timer means and writes the image captured by the camera to the storage means as a still image. While the dispensing-related target object exists, the writing control means writes a moving image or a time-serial image, which is obtained by recording serial works in time series as a plurality of still images, to the storage means.

According to the present invention, if the existence of the dispensing-related target object is confirmed by determining whether the target object exists, the image captured by the camera is associated with the time information of the timer and is written to the storage means as a still image. Further, while the target object exists, the image captured by the camera is written to the storage means as information of a moving image. Thus, the images, in which the situation of dispensing work is recorded, can be retrieved and displayed based on the time information, and the situation of the prescription and the handed medicine can be recognized. Accordingly, concordance and discordance between the prescription and the handed medicine can be readily determined at a later date.

DETAILED DESCRIPTION

Descriptions will be made as to embodiments of the present invention with reference to the accompanying drawings. Like or corresponding components in the drawings are denoted by the same reference numeral and the description thereon will not be repeated in order to avoid repetitive description.

Figure 1:
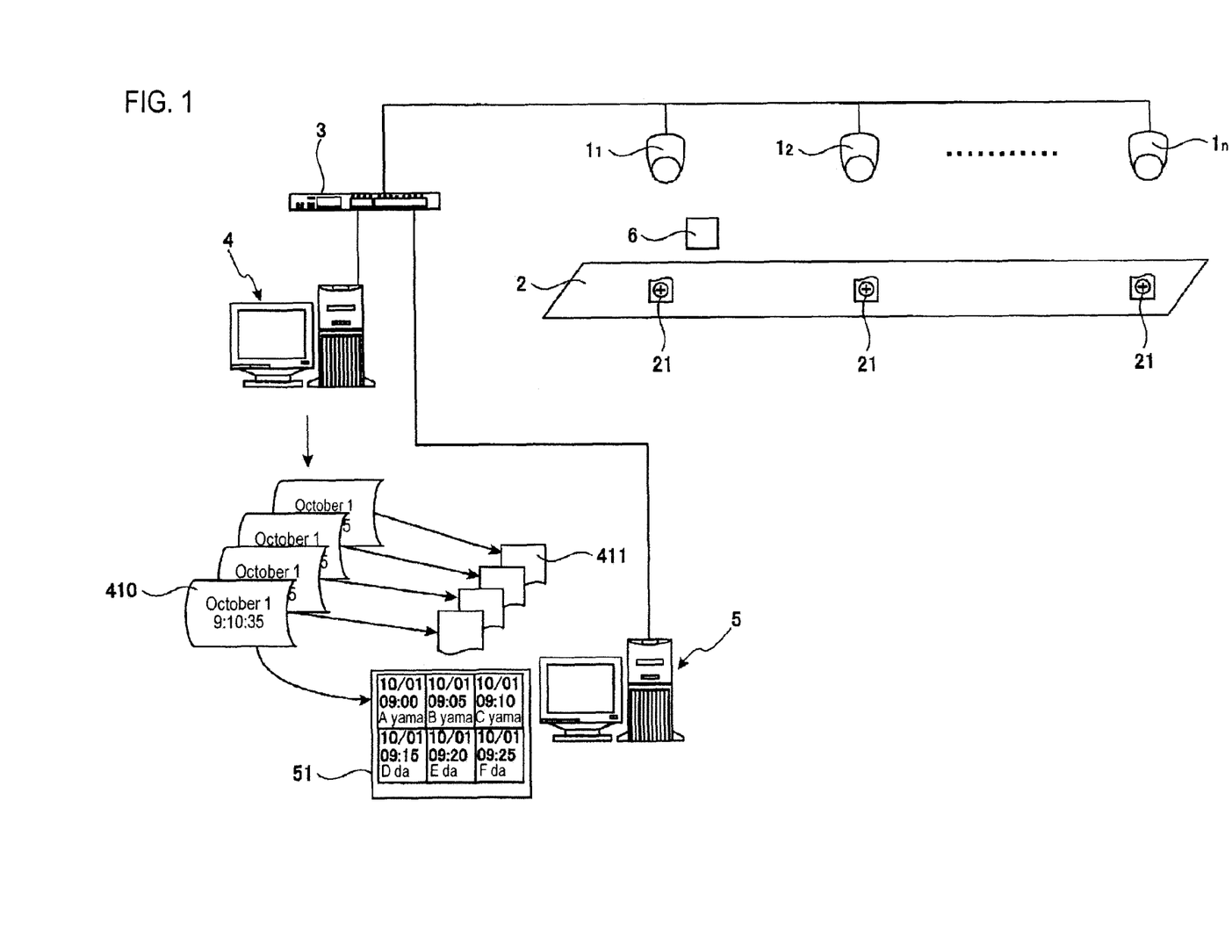
FIG. 1 is a schematic diagram showing an overall configuration of a dispensing verification device of the present invention.

FIG. 1 is a schematic diagram showing the overall configuration of a dispensing verification device of the present invention. As shown in FIG. 1, to photograph a dispensing work performed on a counter 2, a plurality of cameras $1_1$, $1_2$, $1_n$ are installed in a ceiling. These cameras $1_1$, $1_2$, $1_n$ comprise a WEB camera and are connected to a network 3. In FIG. 1, the number of the installed cameras is n, but as many cameras as the number of medicine distribution locations of the counter 2 may be installed. That is, when one pharmacist distributes a medicine to a patient at one location, one camera may suffice. When a plurality of pharmacists can deal with patients at a plurality of locations at the same time, the cameras may be installed at each location where the pharmacist deals with the patient.

In this embodiment, a mark 21 for image recording is provided at the medicine distribution location of the counter 2. The camera $1_1$ . . . photographs the image recording mark 21 and an image data therefrom is given to an image management server 4 via a network 3.

The image management server 4 is connected to the network 3. The distribution of a medicine to a patient is stored in the image management server 4 in association with time as a still image and a moving image, as described below. The image management server 4 saves the images for every date and start time.

As described above, in this embodiment, if the mark 21 is covered and hidden by a prescription 6, then it is determined that a dispensing-related target object exists on the counter. If it is determined that the dispensing-related target object exists on the counter, then an operation of allowing the image management server 4 (image recording device 41) to store the images captured by the camera 1 starts. That is, the image captured by the camera 1 is recognized. If the mark 21 is covered and hidden by the prescription 6 and thus an image excluding the mark 21 is recognized, it starts to record the image captured by the camera 1 as a still image for retrieval and a moving image, or to record the image captured by the camera in a time series as a plurality of still images, for example, in the format of a so-called slide show every second.

In this embodiment, the retrieval still image, the moving image file or the still image file of the format of a slide show is stored in the image management server 4 (image recording device 41). For example, component video signals captured by the camera 1 having a shooting speed of 30 frames/second are converted into digital signals and the digital signals are compressed in a predetermined format into said moving image file. The still image and the moving image are recorded as associated with the date and time of the recording. Herein, "still image" means one image frame and "moving image" means that a plurality of image frames are recorded in succession. The prescription and a scene of handing a medicine to a patient are recorded in the moving image or the still image of the format of a slide show. Regarding the image file, a retrieval still image file 411, wherein an image file after a few seconds from the start (e.g., after five seconds for stabilization of the captured image) is set as a still image, and the moving image file 410 are stored as associated with each other. Further, depending upon the storage capacity of the image management server 4 and the user's demand, the images to be stored in the image management server 4 can be variously selected (e.g., the still image and the moving image, the still image and the slide show format still image) except the retrieval still image. Further, considering the storage capacity, the moving images recordings may be variously selected, for example, by sampling the image file of 10 frame/sec.

A terminal device 5, which is configured to retrieve and display the corresponding information when a patient makes an inquiry, is connected to the network 3. The terminal device comprises a personal computer. The terminal device 5 retrieves the retrieval still images stored in the image management server 4 based on the date and time information. Further, the terminal device 5 extracts and reads out the corresponding still image and then outputs the same to a display device 51 which comprises an LCD. The display device 51 displays the retrieval still image and the corresponding moving image.

Figure 2:
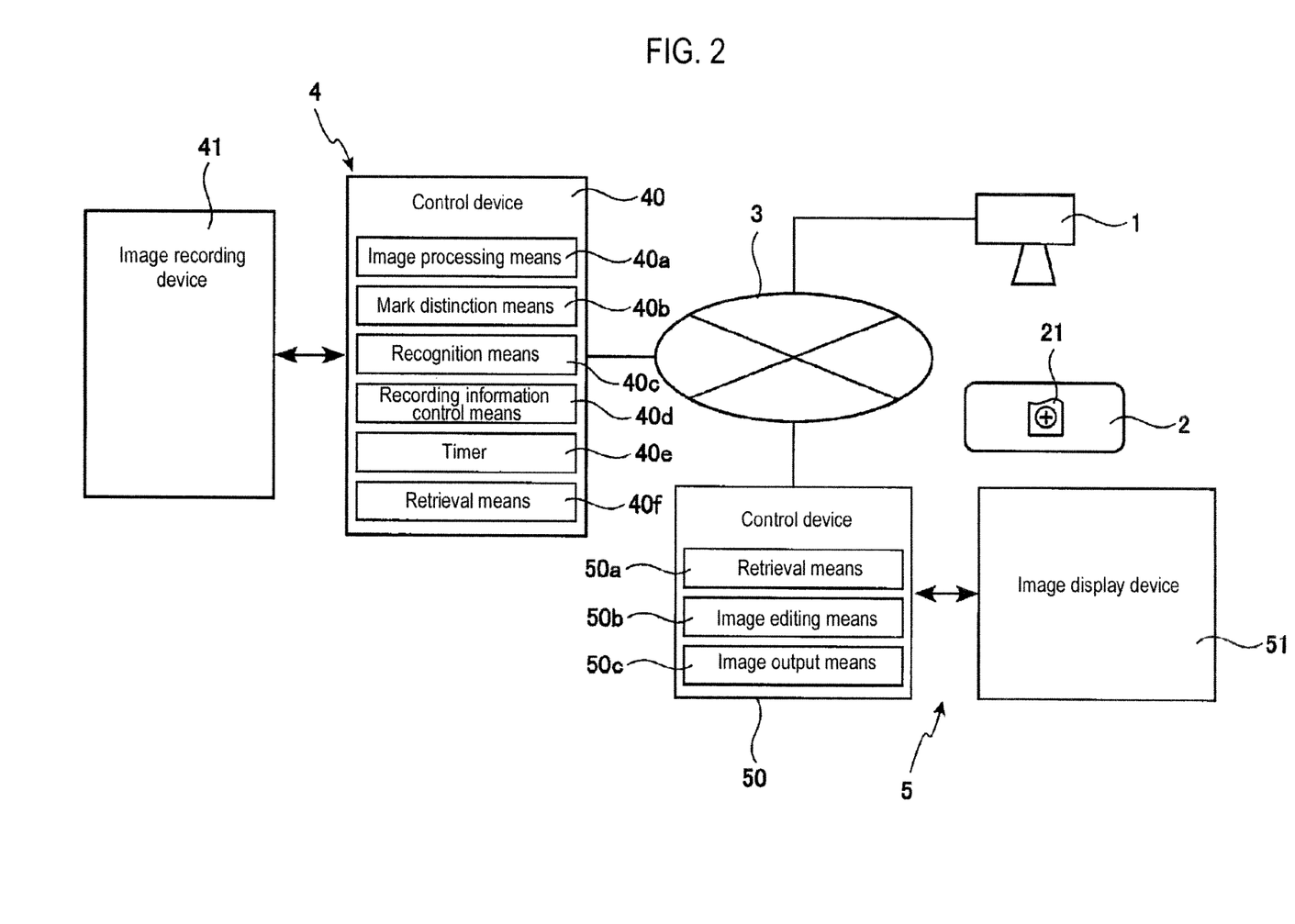
FIG. 2 is a functional block diagram of a dispensing verification device of the present invention.

Descriptions will be made as to the configuration of the dispensing verification device of the present invention with reference to a functional block diagram shown in FIG. 2. In FIG. 2, the image management server 4 is constructed as an information processing apparatus using a personal computer (PC), a workstation or the like. The image management server 4 comprises: the image recording device 41 including a hard disk; and a control device 40 having a control part comprising a CPU, an internal storage device including a ROM, a RAM, etc. The image management server includes: a display device comprising an LCD; an input device including a keyboard, a mouse or the like; and a network processing part connected to the network 3 and performing communication control, which are not shown in FIG. 2. The control device 40 in FIG. 2 performs various functional operations by means of the programs stored in a ROM. In this embodiment, the functions of the control operations performed by the control device 40 are represented as functional blocks.

The camera 1 captures the distribution location of the counter 2 and the captured image data is given to the image management server 4 via the network 3. FIG. 2 shows only one camera 1. In the case of using a plurality of cameras, however, the plurality of cameras are connected to the network 3. Further, in the case of using a plurality of cameras, an ID is given to each camera so that each camera can be distinguished. Further, the image management server 4 is configured to recognize which of the cameras the image comes from.

Figure 3:
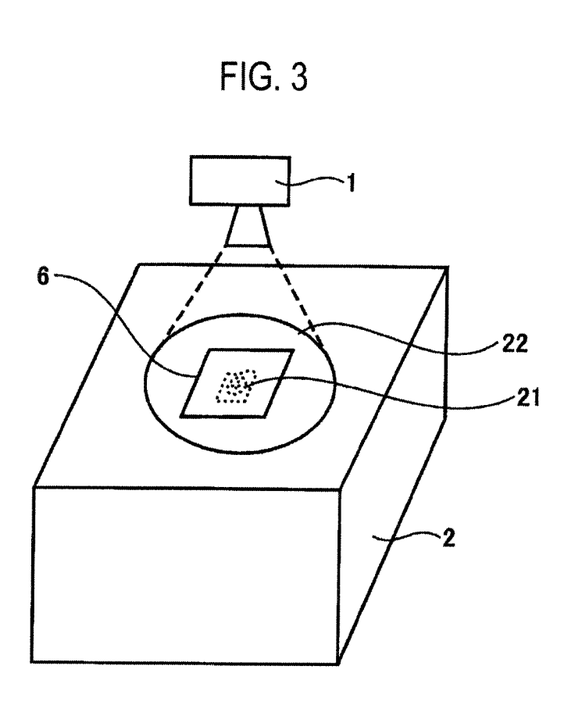
FIG. 3 is a schematic diagram showing a capture area of a camera in a dispensing verification device of the present invention.

FIG. 3 is a perspective view showing a portion of the counter 2, the image of which is captured by the camera. The camera 1 photographs a work area 22 of the counter 2. The mark 21 for recognizing image recording is provided in the central portion of the work area. The mark 21 is hidden by placing the prescription 6 on the mark 21.

As described above, the counter 2 is provided with the mark for recognizing image recording. The image data obtained by capturing the mark 21 is given to the control device 40 of the image management server 4 via the network 3.

The control device 40 introduces the image data, which is inputted from the network 3 to the image processing means 40a. The image processing means 40a performs the following processes: buffering the input image data to the internal storage device; and converting the buffered image into a format suitable for recognition of an image pattern or into a data compression format suitable for image recording by correcting the buffered image by using distortion correction or an image processing technology.

The image file processed through the image processing means 40a is stored in the internal storage device. In this embodiment, as a determination means to determine whether the dispensing-related target object exists on the counter, a mark distinction means 21 is used to determine whether or not the captured image includes the mark 21. The mark distinction means 40b reads out the captured image stored in the internal storage device and determines whether or not the captured image includes the mark 21. The determination information from the mark distinction means 40b is given to a recording information control means 40d. In the state where it is determined that the mark 21 is included, the recording information control means 40d does not give the image file from the camera 1, which is processed through the image processing means 40a, to the image recording device 41, and thus recording in the image recording device 41 does not start.

The internal storage device of the image processing means 40a sequentially rewrites the image files sent from the camera 1.

A timer 40e outputs a date and time information of the system. The date and time information is given to the recording information control means 40d.

A recognition means 40c recognizes the image given from the image processing means 40a. By way of example, when the image is a bar code, the recognition means recognizes the bar code and gives the information contained in the bar code to the recording information control means 40d. Further, when the image is composed of characters, the recognition means 40c recognizes the characters and gives the recognition results, such as a patient's name, to the recording information control means 40d. This embodiment is configured such that the recognition means 40c and the mark distinction means 40b are separate. However, the recognition means 40c may be configured to recognize the image of the mark 21 and the recording information control means 40d may be configured to start or stop recording based on this recognition result. This may eliminate the need to individually configure the mark distinction means 40d.

A retrieval means 40f reads out the image file from the image recording device 41 based on the time information and the patient information associated with the image file stored in the image recording device 41, and outputs the image file to the network 3 and gives the same to the terminal device 5.

If the mark distinction means 40b does not recognize the mark 21, that is, if the prescription 6 is placed on the mark 21, then the mark distinction means outputs to the recording information control means 40d the information that the dispensing-related target object exists.

Upon obtaining the information that the dispensing-related target object exists from the mark distinction means 40b, the recording information control means 40d performs the operation of allowing the image recording device 41 to store the image file. First, the still image file, after a few seconds (e.g. after five seconds for stabilization of captured image) from obtaining the information that the dispensing-related target object exists from the mark distinction means 40b, is stored in the image recording device 41.

When the time information, the patient's name information, etc., are recognized with respect to the still image file during recording in the image recording device 41, the still image file is stored as associated with the recognized data.

Figure 4:
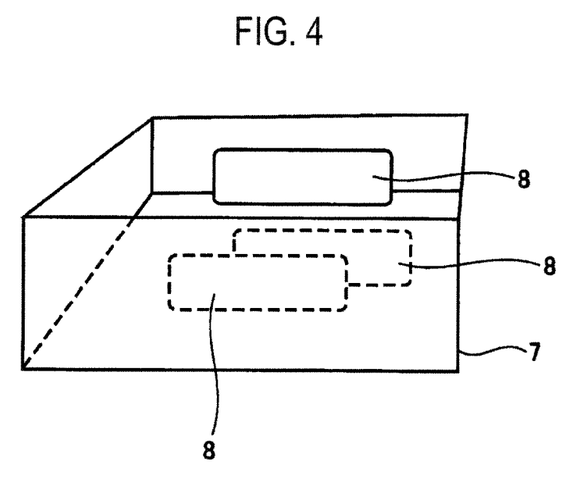
FIG. 4 is a schematic diagram showing a carrier used in a dispensing verification device of the present invention.
Figure 5:
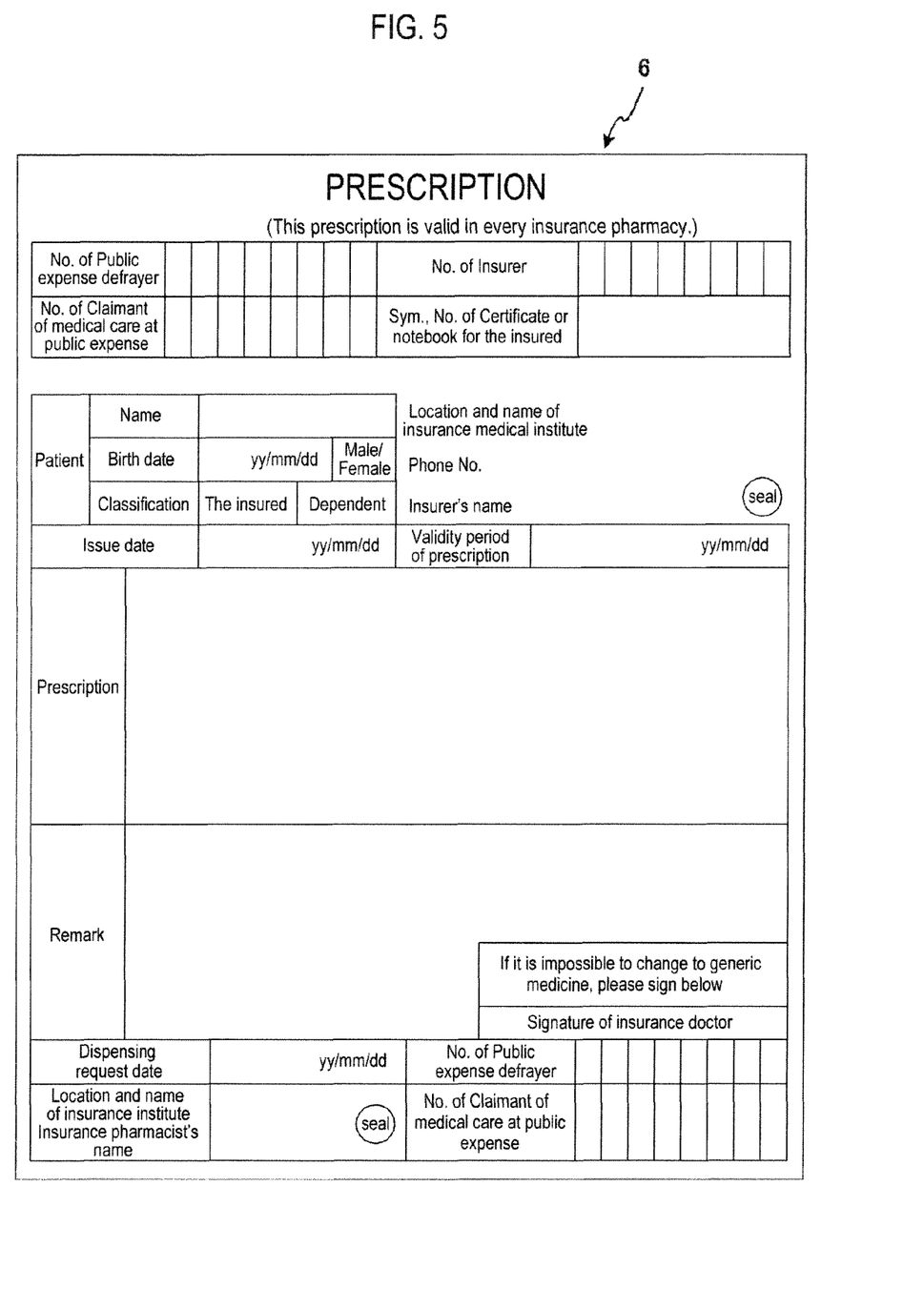
FIG. 5 is a diagram showing an example of a prescription.
Figure 8:
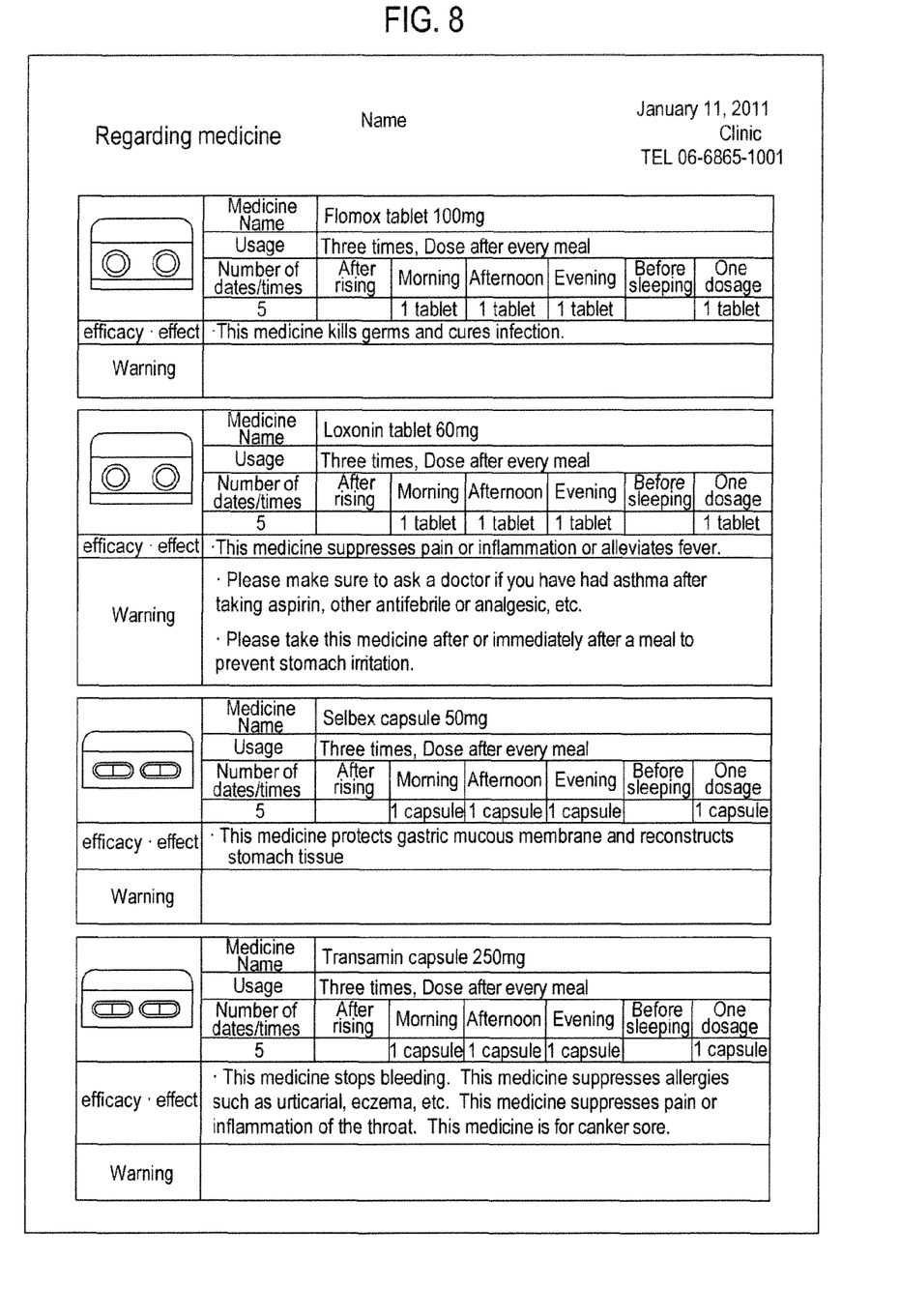
FIG. 8 is a diagram showing an example of a medicine information.

FIG. 4 is a perspective view showing a carrier 7 in which the medicine 8 is placed. The medicine 8 is placed in the carrier 7 along the prescription 6 and the carrier 7 with the medicine placed therein are placed on the counter 2. In accordance with the medicine information shown in FIG. 8, a pharmacist describes the prescribed medicine to the patient and puts the medicine in a medicine bag. The images in connection with these serial acts are recorded in the image recording device 41 of the image management server 4. It starts to record the serial acts as a moving image or as a plurality of time-serial still images in the format of a so-called slide show. When the time information and the patient's name information are recognized with respect to the moving image file or the time-serial image file, the moving image file or the time-serial image file is recorded as associated with the recognized data. The prescription and the scene of handing the medicine to a patient are captured in the moving image file or the images wherein said serial acts are recorded as a plurality of time-serial still images in the format of a so-called slide show. If the medicine is handed to a patient and the mark distinction means 40b detects the mark 21, then the result is given to the recording information control means 40d. By the detection of the mark 21, the recording information control means 40d ends recording and sending the image file to the image recording device 41.

The still image file and the moving image file are saved in the image recording device 41 for each date and start time. Further, when specific information, such as a patient's name, exists through a reading of a bar code, the image recognition or the like, the still image file and the moving image file are stored as associated with the recognized information.

The terminal device 5 is constructed as a personal computer (PC). The terminal device comprises: a control device 50 comprising a control part having a CPU, an internal storage device including a ROM, a RAM, etc.; and a display device 51 comprising an LCD. The terminal device includes: an input device including a keyboard, a mouse or the like; and a network processing part connected to the network 3 and performing communication control, which are not shown in FIG. 2. The control device 50 in FIG. 2 performs various functional operations by means of the programs stored in a ROM. In this embodiment, the functions of the control operations performed by the control device 50 are represented as functional blocks.

When a patient makes an inquiry, a retrieval means 50a creates a retrieval condition based on the information inputted through the input device, such as the time at which a pharmacy staff hands a medicine to the patient, the patient information, the date and time, etc. The retrieval condition is given to the image management server 4 via the network 3. The image management server 4 reads out the corresponding still image file from the image recording device 41 according to the retrieval condition and the data related thereto is given to the terminal device 5 via the network 3. The pharmacy staff searches for the prescription by the patient's testimony or by the patient's name. The pharmacy staff estimates the time when the medicine was handed to the patient based on the time printed on the prescription and then enters the same as the retrieval condition.

Figure 7:
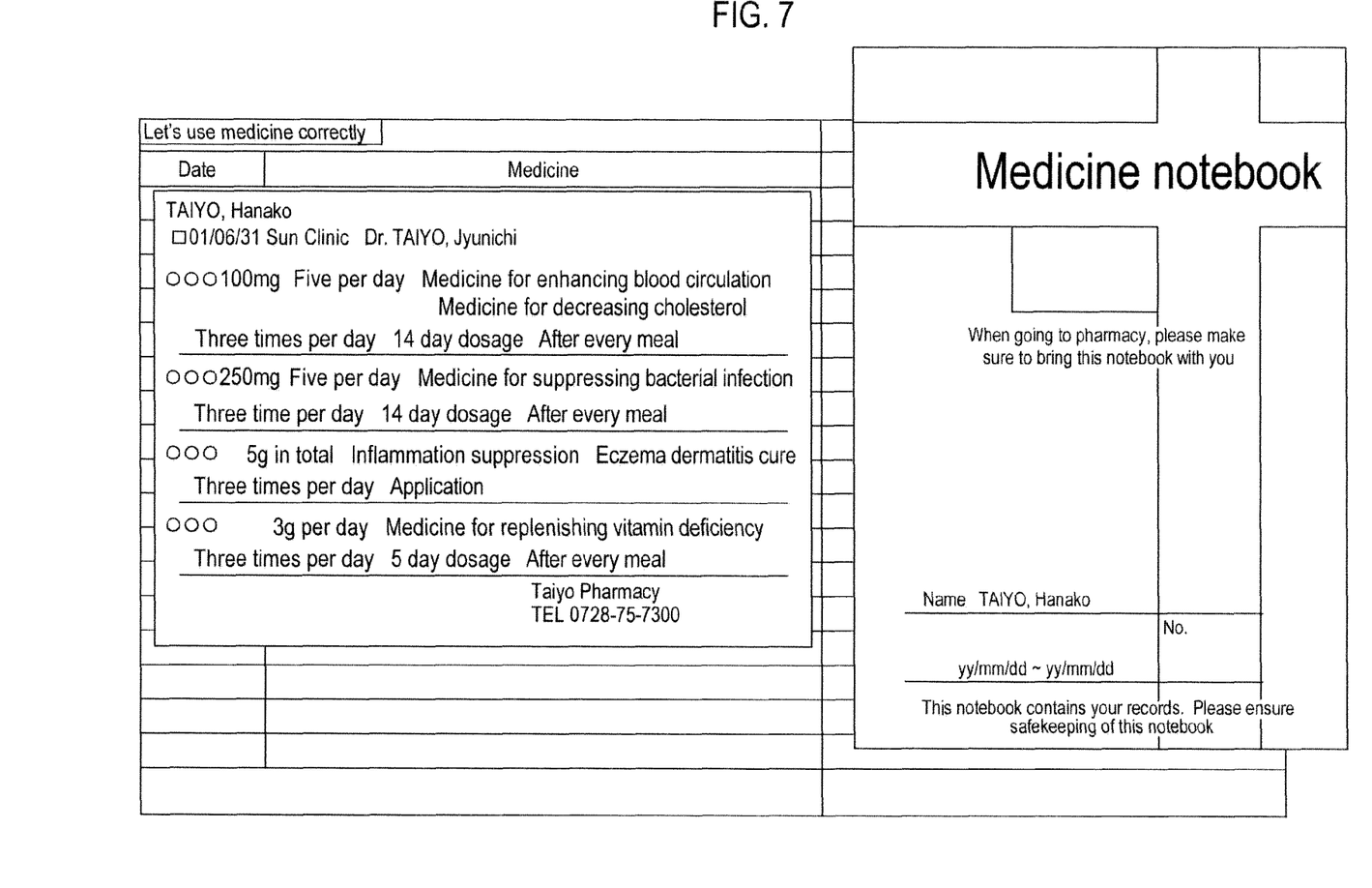
FIG. 7 is a diagram showing an example of a medicine notebook.

In the case where the patient brings the medicine information shown in FIG. 7 when entering the retrieval condition, the retrieval condition is specified by identifying the date and estimating the time based on the data contained in the medicine information.

Figure 6:
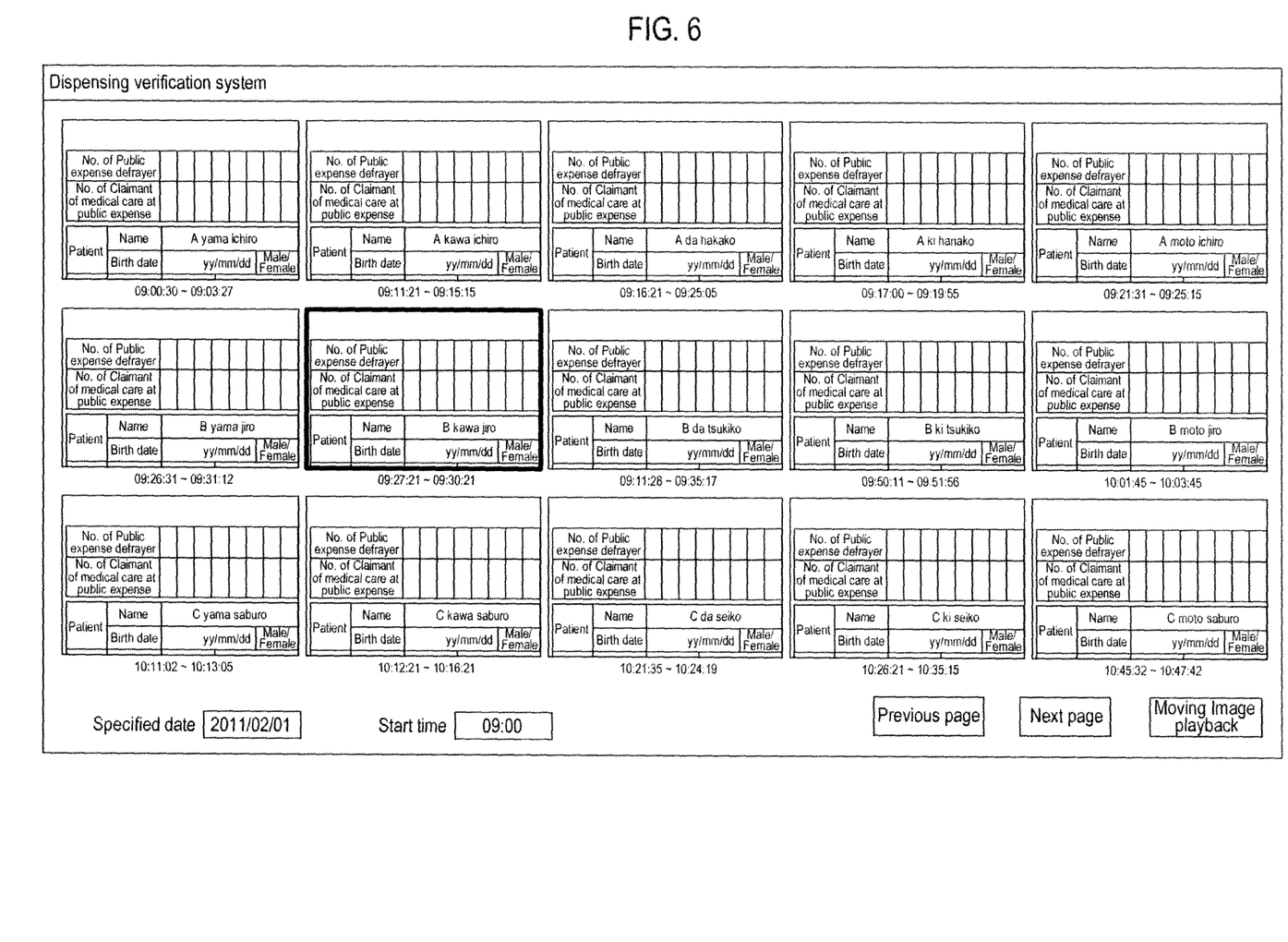
FIG. 6 is a diagram showing a retrieval screen for identifying a patient.

When receiving the corresponding still image file, the terminal device 5 edits a plurality of the retrieval still image files existing before and after the estimated time by using an image editing means 50b so that they can be displayed all at one time in chronological order, and then gives the plurality of the retrieval still image files to an image output means 50c. The image output means 50c outputs the plurality of the retrieval still image files existing before and after the estimated time to the image display device 51 such that the patient information in the prescription is extracted and displayed. As shown in FIG. 6, a plurality of thumbnail images, wherein the area identified by at least the patient's name information and the date and time information is extracted and reflected, are displayed in the image display device 51.

In the example shown in FIG. 6, the retrieval still images for fifteen persons are displayed. The time recording is started and the time recording is stopped are displayed below each still image. As such, the still images before and after the estimated time are displayed on the same screen. Thus, when an exact time cannot be identified, the image can be readily specified since the still images captured before and after the estimated time are displayed all at one time. Further, the number of the still images displayed on the image display device 51 is not limited to fifteen persons shown in FIG. 6. The number of the still images can be set to any number by the user, for example, four persons, twenty persons, etc. The size of the displayed still image may be appropriately changed depending upon the number of persons to be displayed. Further, when all the retrieval still images to be retrieved are not displayed in one screen, such still images may be displayed throughout several pages and such display may be switched by clicking on a previous page area in the screen or a next page area in the screen using a mouse.

Further, in the case where the still images displayed through retrieval do not relate to the corresponding patient, if the pharmacy staff dealing with the patient displays a first page of a retrieval time and then clicks on the previous page area, the retrieval still images, which are for a predetermined time prior to the estimated time for starting retrieval, may be displayed. Similarly, if the pharmacy staff dealing with the patient displays a final page of the retrieval time and then clicks on the next page area, the retrieval still images, which are for a predetermined time posterior to the estimated time for starting recording, may be displayed. With the above-described configuration, it is possible to retrieve the images for the corresponding patient without re-input of the estimated time.

Figure 9:
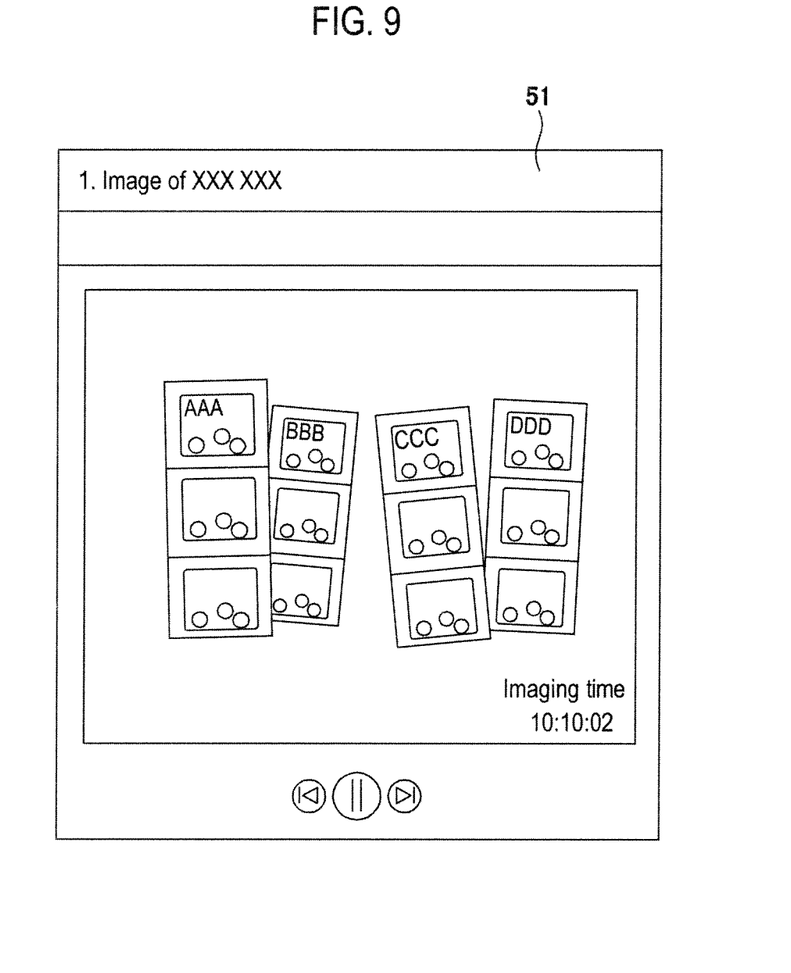
FIG. 9 is a schematic diagram showing an example of a retrieved image.

When the retrieval still image capable of identifying the patient is found, an area of a moving image playback is clicked on and then the moving image file corresponding the still image are requested from the image management server 4. By way of example, "B Kawa Jiro" in the image of 9:27:21 to 9:30:21 in the example shown in FIG. 6 is the patient in question. The area related to said patient is specified and then the playback of the moving image file is requested. The image management server 4 outputs the requested moving image file or the still images of the plurality of time-serial still images (where the serial acts are recorded as a plurality of time-serial still images in the format of a so-called slide show) and then gives the same to the terminal device 5. In the terminal device 5, the display device 51 displays the state of the handover of the medicine to the patient. Thus, it can be judged whether the medicine was provided as it was prescribed. Further, where necessary, the image of the medicine handed to the patient may be displayed in the form of a still image, as shown in FIG. 9. Further, this image may be shown to the patient and the patient can recognize that there was no mistake in dispensing the medicine. As shown in FIG. 9, the imaging time information is simultaneously displayed in said image. By confirming the imaging time information, it can be more clearly determined that there was no mistake in the prescription of the medicine handed to the patient at that time. If there was any mistake in the prescription of the medicine, correctly dispensed medicine may be handed to the patient.

Further, if the prescription is correct, the patient may be directed not to take several medicines by mistake.

Further, the ID of the pharmacist may be affixed to the prescription by a clip and the camera 1 may capture the prescription. Once reviewing the image file, the pharmacist in charge can be found.

When a bar code including date, time, receipt number, patient's ID, patient's name, birth date, etc., is printed on the prescription, the image file may be stored as associated with the information included in the bar code printed. If such association is made, then the information of a patient may be displayed all at one time in the form of a table instead of displaying the image files during retrieval in the terminal device 5. Further, the information of a patient may be sorted by the patient's name and thereby the data related to the patient having an unclear date can be readily retrieved.

Figure 10:
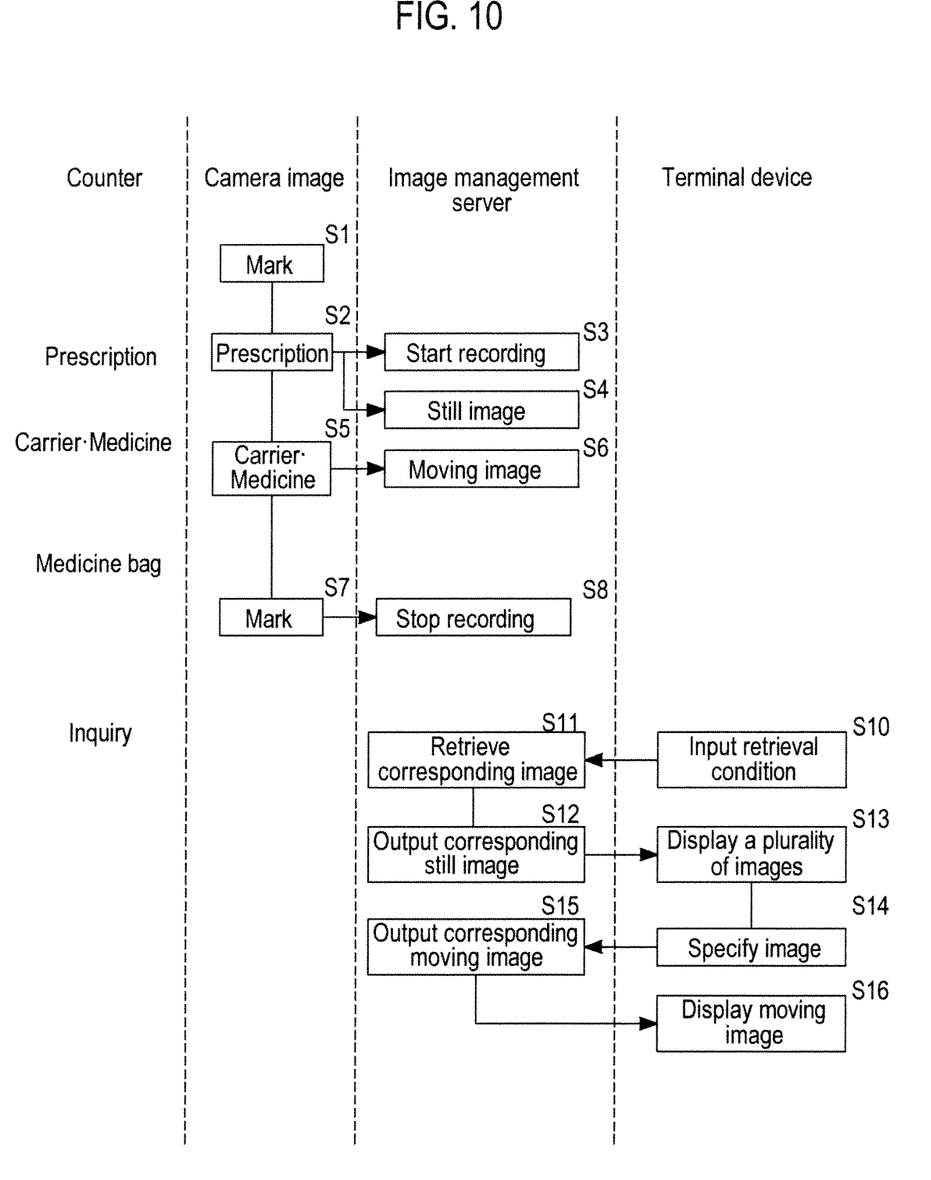
FIG. 10 is a diagram showing correlation between a state of a counter, a camera image, an image management server and a terminal device.

Next, descriptions will be made as to the operations of the dispensing verification device of the present invention with reference to FIG. 10. The camera 1 captures the camera-captured area of the counter 2. If nothing is placed on the work area of the counter 2, the camera 1 outputs the image of the mark 21 for image recording recognition (S1). If the prescription 6 is placed on the mark 21 in the counter 2, then the image of the prescription 6 (S2) is outputted from the camera 1. The mark distinction means 40b determines that the dispensing-related target object exists on the counter 2, and gives the determination result to the recording information control means 40d.

Upon obtaining the information that the dispensing-related target object exists from the mark distinction means 40b, the recording information control means 40d of the image management server 4 starts recording and performs the operation of allowing the image recording device 41 to store the image file. First, a still image file is stored in the image recording device 41 after a few seconds from obtaining the information that the dispensing-related target object exists from the mark distinction means 40b. If a time information, a patient's name information, etc., are recognized during recording in the image recording device 41, the still image file is stored as associated with the recognized data. Subsequently, the camera 1 outputs the images related to the description of the medicine to be handed to the patient and putting the medicine in a medicine bag (S5). The images related to those serial acts are recorded in the image recording device 41 of the image management server 4 as a moving image or as an image obtained by recording those serial acts in a time series as a plurality of still images in the format of a so-called slide show (S6). If the time information or the patient's name information is recognized with respect to the moving image file or the image obtained by recording the serial acts in a time series as a plurality of still images in the format of a so-called slide show, the moving image file or the time-serial image is recorded as associated with the recognized data.

The medicine is handed to the patient and the camera 1 outputs the image of the mark (S7). If the mark distinction means 40b detects the mark 21, then the mark distinction means gives the determination result to the recording information control means 40d, thereby ending the recording of the image file in the image recording device 41.

When the patient makes an inquiry, the pharmacy staff inputs the time at which the medicine is handed to the patient, the patient information and the date and time by using the input device of the terminal device 5 (S10). The retrieval condition is created based on the above-mentioned information and is given to the image management server 4 via the network 3 (S11). The image management server 4 reads out the corresponding still image file from the image storage recording device 41 according to the retrieval condition (S12) and the data related thereto is given to the terminal device 5 via the network 3.

Upon receiving the corresponding still image file, the terminal device 5 edits a plurality of still image files existing before and after the estimated time by using an image editing means 50*b* so that they can be displayed all at one time in chronological order. The image display device 51 displays the still images as a plurality of thumbnail images, wherein the area identified by at least the patient's name information and the date and time information is extracted and reflected (S13).

If the still image file capable of identifying the patient is found, then the moving image file corresponding to the still image file are requested from the image management server 4 (S14). The image management server 4 outputs the requested moving image file or the image file obtained by recording the serial acts as a plurality of still images in a time series in the format of a so-called slide show, and gives the same to the terminal device 5 (S15). Then, in the terminal device 5, the display device 51 displays the delivery state of the medicine to the patient (S16).

In the foregoing embodiment, as a determination means determining whether or not the dispensing-related target object exists on the counter 2, the mark 21 for image recording is provided at the medicine distribution location of the counter 2 and the existence of the target object is determined based on whether or not the mark 21 is recognized. Further, writing the images of the camera 1 in the image management server 4 is controlled based on whether or not the mark 21 is recognized. However, the aforesaid determination means that determines whether or not the dispensing-related target object exists on the counter is not limited to the foregoing. For example, instead of providing the mark 21 on the counter 2, the prescription 6 is placed in the work area 22 of the camera 1 and the image from the camera 1 may be recognized. If the recognition result is the prescription 6, then it may be determined that the dispensing-related target object exists on the counter 2, in which case the images from the camera 1 begins to be written in the image management server 4. Further, if the images from the camera 1 relates to only the status of the counter 2 for at least a predetermined time, then it may be determined that the dispensing-related target object does not exist on the counter 2, in which case the images from the camera 1 stops being written in the image management server 4.

Further, as the determination means that determines whether or not the dispensing-related target object exists on the counter 2, the determination of whether the dispensing-related target object exists on the counter 2 may be made by using a reflective type sensor instead of the images from the camera 1.

Further, the pharmacist may push a record start button when the pharmacist hands a medicine to a patient and may push a record stop button when the handing over of the medicine is complete. In this way, it may be determined whether or not the dispensing-related target object exists on the counter 2.

It should be understood that the embodiments disclosed herein are illustrative in all respects and is not in any way limiting. The scope of the present invention is defined by the appended claims rather than by the description of the foregoing embodiments, and is intended to cover all modifications falling within the meanings and scopes equivalent to the claims.

DESCRIPTION OF REFERENCE NUMERALS

1 Camera
2 Counter
21 Mark for image recording
3 Network
4 Image management server
5 Terminal device
6 Prescription

What is claimed is:

1. A dispensing verification device, comprising:
a camera capturing a region of a counter at which a plurality of acts are performed, the region including a mark; and
a server comprising a central processing unit, a non-transitory computer-readable medium, and a display device, the computer-readable medium storing instructions for causing the central processing unit to perform steps including:
for each act of the plurality of acts:
receiving a corresponding image captured by the camera of the region of the counter;
determining whether the mark at the region of the counter is hidden in the received image;
outputting a time information;
storing the received image as a still image in response to determining that the mark at the region of the counter is hidden;
in response to determining that the mark at the region of the counter is hidden in the received image, storing a moving image or series of additional still images captured by the camera of the region of the counter; and
associating the stored image with the time information;
retrieving, based on a time inputted by a user, the still images respectively corresponding to the acts of the plurality of acts, wherein the retrieved still images are thumbnail images of extracted areas each with different patient information than one another;
displaying the retrieved still images at the display device at the same time as one another with the respective time and date of capture of each of the displayed still images;
receiving user input selecting one of the displayed still images corresponding to one of the acts; and
responsive to the user input, displaying the moving image or series of additional still images corresponding to the one of the acts.

2. The dispensing verification device of claim 1, wherein responsive to the user input, the display device simultaneously displays the still images of the series of additional still images corresponding to the one of the acts.

3. The dispensing verification device of claim 1, the computer-readable medium further storing instructions for causing the central processing unit, based upon the displayed still image being selected, to read out data within the moving image or the series of additional still images, and to display the read out data at the display device.

4. The dispensing verification device of claim 1, the computer-readable medium further storing instructions for causing the central processing unit to extract from the selected still image a patient identifying area and to display the patient identifying area at the display device.

5. The dispensing verification device of claim 1, the mark being provided at a medicine distribution location of the counter.

6. The dispensing verification device of claim 1, wherein the mark is hidden by a prescription placed on the region of the counter.

7. The dispensing verification device of claim 6, the computer-readable medium further storing instructions for causing the central processing unit to recognize a patient identifying area in the prescription and to recognize a patient information based on the recognized patient identified area.

8. A dispensing verification method, comprising:
by a camera, capturing a region of a counter at which an act is a plurality of acts are performed, the region including a mark;
for each act of the plurality of acts:
by a server, receiving an image captured by the camera of the region of the counter;
by the server, determining whether the mark at the region of the counter is hidden in the received image;
by the server, outputting a time information;
by the server, storing the received image as a still image in response to determining that the mark at the region of the counter is hidden;
in response to determining that the mark at the region of the counter is hidden in the received image, storing by the server a moving image or series of additional still images captured by the camera of the region of the counter; and
by the server, associating the stored image with the time information;
retrieving, based on a time inputted by a user, the still images respectively corresponding to the acts of the plurality of acts, wherein the retrieved still images are thumbnail images of extracted areas each with different patient information than one another;
by the server, displaying the retrieved still images at a display device at the same time as one another with the respective time and date of capture of each of the displayed still images;
receiving user input selecting one of the displayed still images corresponding to one of the acts; and
responsive to the user input, displaying the moving image or series of additional still images corresponding to the one of the acts.

9. The method of claim 8, comprising, by the server, responsive to the user input, simultaneously displaying the still images of the series of additional still images corresponding to the one of the acts.

10. The method of claim 8, further comprising, based upon the still image being selected, reading out by the server data within the moving image or the series of additional still images, and displaying by the server the read out data at the display device.

11. The method of claim 8, further comprising, by the server, extracting from the selected still image a patient identifying area and displaying the patient identifying area at the display device.

12. The method of claim 8, the mark being provided at a medicine distribution location of the counter.

13. The method of claim 8, wherein the mark is hidden by a prescription placed on the region of the counter.

14. The method of claim 13, further comprising recognizing by the server a patient identifying area in the prescription and to recognizing by the server a patient information based on the recognized patient identified area.

15. The method of claim 8, wherein the associating is performed after a predetermined time after the determining.

16. The dispensing verification device of claim 1, wherein the associating is performed after a predetermined time after the determining.

17. The dispensing verification device of claim 1, wherein the displaying the retrieved still images includes displaying the retrieved still images on the same screen.

18. The method of claim 8, wherein the displaying the retrieved still images includes displaying the retrieved still images on the same screen.

* * * * *